US008963565B2

(12) United States Patent
Pfeiffer et al.

(10) Patent No.: US 8,963,565 B2
(45) Date of Patent: Feb. 24, 2015

(54) SENSOR FOR DETECTING LIQUID SPILLING

(75) Inventors: Helge Pfeiffer, Wezemaal (BE); Martine Wevers, Tongeren (BE)

(73) Assignee: Katholieke Universiteit Leuven, Leuven (BE)

( * ) Notice: Subject to any disclaimer, the term of this patent is extended or adjusted under 35 U.S.C. 154(b) by 232 days.

(21) Appl. No.: 13/809,517

(22) PCT Filed: Jul. 12, 2011

(86) PCT No.: PCT/BE2011/000046
§ 371 (c)(1),
(2), (4) Date: Jan. 10, 2013

(87) PCT Pub. No.: WO2012/006692
PCT Pub. Date: Jan. 19, 2012

(65) Prior Publication Data
US 2013/0113505 A1     May 9, 2013

Related U.S. Application Data (60) Provisional application No. 61/399,514, filed on Jul. 12, 2010.

(30) Foreign Application Priority Data

May 9, 2011 (GB) .................................. 1107664.3

(51) Int. Cl.
G01R 27/08     (2006.01)
G01N 27/12     (2006.01)
G01R 27/02     (2006.01)

(52) U.S. Cl.
CPC .............. G01N 27/126 (2013.01); G01R 27/02 (2013.01); G01N 27/12 (2013.01)
USPC .......... 324/694; 436/143; 205/777.5

(58) Field of Classification Search
CPC ..... G01N 27/127; G01N 27/12; G01R 27/02; G01R 27/07
USPC ........................................................ 324/694
See application file for complete search history.

(56) References Cited

U.S. PATENT DOCUMENTS 4,635,027 A * 1/1987 Miyoshi et al. ................. 338/34
5,256,574 A * 10/1993 Neuburger et al. ........... 436/143
(Continued)

FOREIGN PATENT DOCUMENTS

DE         19963188 A1    9/2000

OTHER PUBLICATIONS

International Searching Authority: European Patent Office (ISA/EP). International Search Report, International Application No. PCT/BE2011/000046. Jan. 3, 2012.
(Continued)

Primary Examiner — Benjamin M Baldridge
(74) Attorney, Agent, or Firm — The Marbury Law Group, PLLC (57) ABSTRACT

Present invention concerns generally to a sensor or a sensor system for detecting spilling of aqueous liquids, for instance in confined spaces were such is critical such in an airplane. The system of present invention is an early warning system or sentinel for the prevention of corrosion by corrosive liquids. Corrosion caused by corrosive liquids can rapidly change the surface properties of components in engineering structures, and that will finally endanger the functionality of structural parts. However, if monitoring technologies are in place providing continuous information on the presence of corrosive liquids, corrosion treatment and even corrosion prevention can start at a very early stage. Present invention provides such by early detection of corrosive liquids by extended sensors based on the collapse of percolation conductivity (COPC). The term collapse refers to the fact that the transition into the non-conducting state must not necessarily have the properties of a thermodynamically well-defined transition.

17 Claims, 4 Drawing Sheets

(56) References Cited

U.S. PATENT DOCUMENTS

| | | | |
|---|---|---|---|
| 8,797,050 B2 * | 8/2014 | Kitchener et al. | 324/694 |
| 2004/0189331 A1 * | 9/2004 | Girshovich et al. | 324/694 |
| 2005/0150778 A1 * | 7/2005 | Lewis et al. | 205/777.5 |
| 2010/0141281 A1 * | 6/2010 | Johnsen | 324/694 |
| 2012/0098555 A1 * | 4/2012 | Raymond | 324/694 |

OTHER PUBLICATIONS

International Searching Authority: European Patent Office (ISA/EP). Written Opinion of the International Searching Authority, International Application No. PCT/BE2011/000046. Jan. 3, 2012.

* cited by examiner

SENSOR FOR DETECTING LIQUID SPILLING

Related Applications

This application is the U.S. national phase entry under 35 U.S.C. §371 of PCT Application No. PCT/BE011/000046, filed Jul. 12, 2011, which claims the priority benefit of U.S. Application No. 61/399,514, filed Jul. 12, 2010, and of United Kingdom Application No. 1107664.3, filed May 9, 2011. Applications PCT/BE2011/000046, and 61/399,514 and 1107664.3 are incorporated herein by reference in their entirety.

BACKGROUND AND SUMMARY

Background of the Invention

A. Field of the Invention

Present invention concerns generally to a sensor or a sensor system for detecting spilling of aqueous liquids, for instance in confined spaces were such is critical such as in an airplane. The system of present invention is an early warning system or sentinel for the prevention of corrosion by corrosive liquids. Corrosion caused by corrosive liquids can rapidly change the surface properties of components in engineering structures, and that will finally endanger the functionality of structural parts. However, if monitoring technologies are in place providing continuous information on the presence of corrosive liquids, corrosion treatment and even corrosion prevention can start at a very early stage. Present invention provides such by early detection of corrosive liquids by extended sensors based on the collapse of percolation conductivity (COPC). The term collapse refers to the fact that the transition into the non-conducting state must not necessarily have the properties of a thermodynamically well-defined transition.

Several documents are cited throughout the text of this specification. Each of the documents herein (including any manufacturer's specifications, instructions etc.) are hereby incorporated by reference; however, there is no admission that any document cited is indeed prior art of the present invention.

B. Description of the Related Art

Leakage of liquids into the sealed floor beam area in aircraft is normally not monitored in nowadays maintenance operations because the respective structures are hidden and difficult to access. Respective problems can be detected only at regular heavy inspections (D-checks, or heavy maintenance, usually ranging between four and six years) or when corrosion damage gets obvious, when e.g. seats lose mechanical contacts to the seat tracks when the respective structural elements are essentially corroded. A monitoring system would thus enable huge cost savings when the presence of corrosive liquids could be detected at a very early stage.

In principle, various leakage sensors for aqueous liquids could be used to monitor the floor beam. However, the challenge is always the limited space available in the floor beam structure, the difference between baseline variations at normal operations and the signals after ingressing liquids, the price of the instrumentation, certification issues etc. Such monitoring system must accurately detect intrusion or ingression of aqueous liquids spills into or under the floor cover (e.g. the carpet) for instance in the floor beam area. But the monitoring system may not be disturbed for instance by normal variations of the atmospheric humidity in the confined environment above the floor cover.

A publication (U.S. Pat. No. 6,717,664) proposes an optical fibre system to enable the use of a boroscope for inspecting longer distances in the hidden space of the floor beam area. However, this would nevertheless require time-consuming manual inspections and probably not all spaces could be accessed.

In another patent publication (U.S. Pat. No. 6,063,486), a sensor is reported that provides a gradual measure of the humidity when measuring the conductivity of a conductive composite at different water vapour pressures. Such sensor is not suitable for the object of present invention. That sensor is intended to measure the humidity over a broader range, and it focuses on repeatability, fast measuring and sensor stability. In our case, variations of the humidity in the floor beam area is usually limited at normal operations (RH-10-20%), and the ingress of aqueous liquids would immediately cause humidities close to RH-100%, for instance above 75%, preferably above 85%, more preferably above 95%, yet more preferably above 97%, yet more preferably above 99% and most preferably above 99% (see FIG. 1). To discriminate between unimportant baseline variations (change of humidity at normal operations) and the ingress of aqueous liquid, the collapse of percolation conductivity (COPC) is used (see below) that is not mentioned nor exploited in the art. There are also other sensors reported that describe the use of the change of conductivity as a function of the concentration of the conducting particle. It is e.g. well-known that the very hygroscopic salt $LiCl_2$ changes its conductivity as a function of water vapour pressure making resistance measurements of that salt to an interesting tool for measuring humidities.

Areas that are prone to corrosion damage are normally isolated from the wet environment. A typical example is the floor beam area in aircraft; the floor beams are covered by protective coatings, and the joints between floor panels are equipped with sophisticated sealing systems.

However, coatings and sealings can be damaged due to the intensive use of the aircraft. Aqueous liquids arising from spillage (especially in the galley and lavatory area) or from passengers boarding at rainy weather conditions can enter the space between the floor panels, and it is known that this penetration can cause heavy corrosion in the underlying floor structure that is frequently made of aluminium alloys (corrosion is accelerated by galvanic corrosion with composite floor plates). As the regular maintenance of floor beams is scheduled with relatively long periods (usually between four and six years), a starting corrosion problem can remain undiscovered for a long time.

A reliable sensor or sensor network for aqueous liquids which is interrogated in the time frame of days, or even more frequently, could help to the reduce repair costs of floor beams considerably and they can even lead to a reduction of the number of inspections. An important challenge concerning the installation of sensors in the floor beam area is the limited space available. Furthermore, the sensor has to cover an extended area.

In the present invention, a sensor is presented that is based on the transition of the percolation threshold of a composite comprising a conducting compound which is embedded in a hydrophilic matrix. The components are mixed in an appropriate ratio, resulting in a composition so that the composite is above the percolation threshold, i.e. in the conducting state.

When this composite is exposed to water, the system takes up the liquid until the conductivity is essentially lost. The increase of the resistance due to the ingress of water could at a later stage be monitored by a digital multi-channel multimeter that is equipped with appropriate data logging facilities. However, this is not necessary because the sensor "remembers" the ingress of liquids so that the reading-out can be performed by instruments that are not on board. This essentially reduces the certification effort of that technique.

The applicability of the integral system could already be shown in a relevant lab-environment using different aqueous liquids and it is also implemented in an operational airliner.

SUMMARY OF THE INVENTION

In accordance with the purpose of the invention, as embodied and broadly described herein, the invention is broadly drawn to a gauge comprising a sensing material that is a composite comprising at least two components. 1) a dispersed electrically-conductive material b) a lyophilic matrix for embedding the dispersed electrically-conductive material (usually, but not necessarily performed as a polymer). The concentration, dispersion and/or orientation of the electrically-conductive particles are tailored to be as far as possible from the percolation threshold (see gap between operational range "A" and the leakage case "B" in FIG. 1) in a way that the composite itself is always in the electrically-conductive state at normal operations. Finally, the percolation conductivity is essentially interrupted if a relevant amount of solvent (less than 0.5 ml, harmful quantity of aqueous solvents or oily liquids or harmful organic solvents) has entered the lyophilic composite, i.e. the disappearance of conductivity is a consequence of the swelling of the lyophilic embedding matrix (thus by transition through the threshold of percolation conductivity (collapse of percolation conductivity, COPC) into the non-conductive state).

Another aspect of the invention is the transition through a threshold of percolation conductivity (collapse of percolation conductivity (COPC)), instead of a gradual measure of the conductivity for instance as a function of water vapour pressure. The sensor of present invention explicitly uses that collapse of percolation conductivity (COPC), and variations of the conductivity in the conducting state according to the previous sensor just appear as baseline variations in our applications that are not used for sensing purposes. At the COPC, the conductivity changes many orders of magnitude. The final resistance in the non-conducting state can go beyond approximately 100 MOhm (depending on the sensor size), and it is mainly determined by the remaining conductivity of the aqueous phase forming an own percolation network.

In still another aspect of the invention, the sensors function as an electrical safety fuse that after exposing to a harmful event, it loses its conductivity for a sufficient long time.

Some embodiments of the invention are set forth directly below.

An embodiment of present invention concerns a monitor adapted to monitor a floor structure in a confined environment, whereby the monitor comprises a sensing material [1] and at least one electrode [3] for measuring resistance in the sensing material [1], whereby the sensing material [1], which is adapted to detect hidden aqueous liquids and/or corrosive liquids under a carpet or protective cover of an underlying floor structure (e.g. floor beam structure), comprises a composite and the composite comprises at least two components: 1) particles or powder of an electrically-conductive material dispersed in 2) a matrix that is hydrophilic or that is highly solvable to aqueous fluids and whereby the concentration, dispersion and/or orientation of the electrically-conductive particles or powder are tailored to grow resistance until a conductivity percolation threshold after entering of a liquid, for instance spilled liquids or condensation liquids, into the composite.

Figure 1:
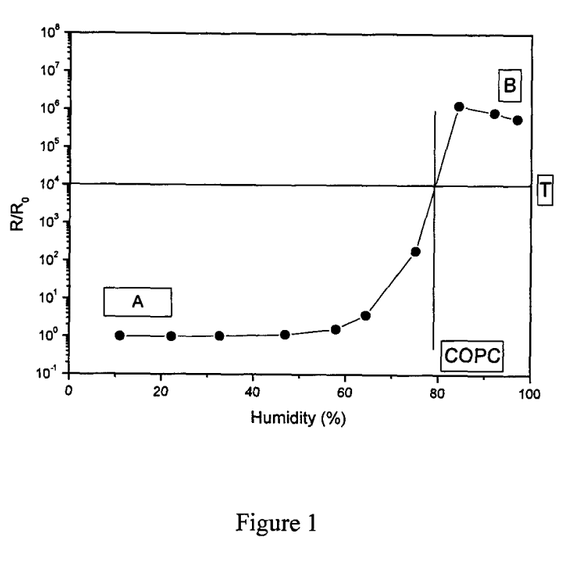
FIG. 1) is a graphic that displays the resistance of the sensor material after step-wise increasing of humidity (RH). "A" indicates the humidity range usually present in airplanes. "B" is the humidity range related to leaking aqueous liquids. "COPC" denotes the collapse of percolation conductivity (note the logarithmic scale). "T" is the possible detection threshold for the sensor (resistance grows by more than factor 1000 above humidity levels for normal aircraft operations). One can see that resistance variations due to varying humidities do not play any role at this scale.

In another embodiment of the monitor according to the invention, the monitor is adapted to monitor a floor structure in a confined environment, whereby the monitor, comprises a sensing material [1] and an electrode or plurality of electrodes [3] for measuring resistance in the sensing material [1], which sensing material [1] is adapted to detect hidden aqueous liquids and/or corrosive liquids, under a carpet or protective cover of an underlying floor structure (e.g. floor beam structure), whereby the sensing material [1] comprises a composite which comprises at least two components: 1) particles or powder of an electrically-conductive material dispersed in 2) a matrix that is hydrophilic or that is highly solvable to aqueous fluids and whereby the concentration, dispersion and/or orientation of the electrically-conductive particles or powder are tailored above a percolation threshold or are tailored to be as far as possible from the percolation threshold (see gap between operational range "A" and the leakage case "B" in FIG. 1) in a way that the composite itself is always in the electrically-conductive state at normal aircraft operations, but has the percolation conductivity interrupted after entering of aqueous liquid into the composite.

According to one aspect of the invention, a monitor is adapted to monitor a floor structure in a confined environment, whereby the monitor, comprises a sensing material [1] and an electrode or a plurality of electrodes [3] for measuring resistance in the sensing material [1], whereby the sensing material [1] is adapted to detect hidden aqueous liquids and/or corrosive liquids, for instance spilled liquids or condensation liquids under a carpet or protective cover of the underlying floor structure (e.g. floor beam structure), characterized in that the sensing material [1] is in the form of a wired sensor and comprises a composite which comprises itself at least two components: 1) particles or powder of an electrically-conductive material dispersed in 2) an matrix that is hydrophilic or that is highly solvable to aqueous fluids with the concentration, dispersion and/or orientation of the electrically-conductive particles or powder being adapted to induce a resistance jump in said composite (the percolation threshold) if part of the wire is exposed to an aqueous liquid (for instance a water drop).

According to another aspect the monitor according to the invention as described above is characterized by any of the following features explained hereunder. The monitor is characterised in that the conductivity percolation threshold is sudden collapse of percolation conductivity. The monitor is characterised in that the resistance grows until a conductivity percolation threshold is reached followed by a consequent sudden collapse of percolation conductivity. The monitor is characterised in that said monitor does not changes its conductivity as a function of water vapour pressure in a confined environment above the carpet or protective cover of floor beams. The monitor is characterised in that collapse of percolation conductivity or sudden increase of the resistance is only due to the ingress of aqueous liquid when its composite is exposed to the aqueous liquid. The monitor is characterised in that the conductivity is essentially lost when the sensing material [1] placed under the carpet or protective cover of the floor beams takes up the liquid. The monitor is characterised in that it is insensitive to an alteration of the atmospheric humidity or the water vapour above the carpet or protective cover of floor beams. The monitor is characterised in that the monitor is insensitive to humidity variations of RH=10-20%. The monitor is characterised in that the monitor is insensitive to humidity variations under 70%. The monitor is characterised in that ingress of aqueous liquid into the floor structure causes collapse of percolation conductivity in said sensing material of said monitor. The monitor is characterised in that the concentration, dispersion and/or orientation of the electrically-conductive particles or powder is in a way that the composite itself is normally in the electrically-conductive state but has the percolation conductivity interrupted after entering of aircraft aqueous fluid into the composite of said sensor detects ingress of aqueous liquid or humidities of at least RH=80% under a carpet or protective cover of floor beams but is relatively insensitive to moisture or humidity variation in the atmosphere of the aircraft above the carpet or protective cover of floor beams of said aircraft. The monitor is characterised in that the monitor is characterised in that the concentration, dispersion and/or orientation of the electrically-conductive particles or powder is in a way that the composite itself is normally in the electrically-conductive state but has the percolation conductivity interrupted after entering of aircraft aqueous fluid into the composite of said sensor detects ingress of aqueous liquid or humidities close to RH=100% under a carpet or protective cover of floor beams but is relatively insensitive to moisture or humidity variation in the atmosphere of the aircraft above the carpet or protective cover of floor beams of said aircraft. The monitor is characterised in that the monitor operates real-time. The monitor is characterised in that the sensing material forms a sensor or sensors. Or the monitor is characterised in that the sensing material forms an in situ sensor or in situ sensors.

It is an object of the invention to realize an aircraft monitor and more particularly an aircraft floor monitor to protect said aircraft from destruction by ingress of water or watery fluid under the floor cover. Experiments showed that the above described monitors are perfectly suited for this function.

According to another aspect the monitor according to the invention as embodied in the description above is in a particular embodiment characterized in that the confined environment is an area in an aircraft and the floor structure is the sealed floor beam area in the aircraft. Such confined environment can be a passengers room, a cargo room or a cockpit room in an aircraft.

According to other aspect of the invention, the monitor according to any of the above mentioned embodiments comprises a sensing system of elongated sensors, sensor tubings, sensor cables, cord sensor or sensor fibres. Such sensing system in a particular embodiment comprises a multiple sensor arrangement. The multiple sensor arrangement can form an array for instance a regular periodic array.

Other aspects of present invention concern different sensing system arrangements that can be features of such monitor described above. For instance the sensing system comprises sensing fibre channels; or the sensing system a multiple fibre arrangement, the multiple fibre arrangement can form a net. Another aspect of present invention concerns specific features of the elongated sensor so can the elongated sensors be coated by an isolating coating or a fabric [2] that is permeable for the aqueous liquids, for instance a coating comprising nylon cord; the elongated sensors can be channelled in liquid collecting sinks in the floor or between the floor plates above the floor beams; the elongated sensors can be attached to the floor carpet or the floor protection; the elongated sensors can be integrated in the floor carpet or the floor protection; the elongated sensors can be multicore sensor cord cables each sensor cord having a different percolation threshold. Preferably the isolating coating of said sensor core does not resist an attack by spilled corrosive fluids.

In addition or as an alternative thereto, the monitor according to the embodied invention described above, comprises sensors which are elongated sensors, sensor tubings, sensor cables, cord sensor or sensor fibres and the eventually elongated sensors are multicore sensor cord cables and eventually elongated sensors are multicore sensor cord cables each sensor cord having a different percolation threshold which sensors are incorporated in a tape, sheet or fabric for attaching to a surface for instance an the aircraft floor such to capture into the sensing materials the spilled aqueous liquids.

A preferred embodiment of the monitor according to the invention is characterized in that the conductivity of the sensing material is interrupted as consequence of the absorption of the aqueous fluid into the matrix embedding the electrically-conductive material powder or particles by transition through the threshold of percolation conductivity (collapse of percolation conductivity into the non-conductive state).

The invention furthermore relates to a monitor according to any of the above described embodiments 1) whereby the conductive particles are of the group consisting metal particle (which can be the metal particle is nickel, cupper or silver or a particle coated with nickel, cupper or silver), a particle coated by said metal, a carbon black particles and particles of conductive ceramics or 2) whereby the conductive particles are a titantiumcarbonitride (TiCN) powder.

In accordance with another development of the invention, the monitor according to any of the above described embodiments, comprises a matrix which is a hydrophilic matrix. For instance the matrix comprises a polymer that is hygroscopic, or the matrix comprises polyvinyl alcohol and/or the matrix swells when it is exposed to a liquid water phase.

According to one aspect of the invention, in the monitor of present invention after exposure to aqueous liquid the resistance in the composite increases which can be displayed on a screen after processing in that the curve of resistance (Ohm) vs. time (min) shows an increase in the resistance.

Other component choices are these whereby the monitor of present invention comprises elongated sensors whereby the integral length of the elongated sensors, sensor tubings, sensor cables, cord sensor or sensor fibres has 2 m or more than 0.2 m; whereby the diameter of elongated sensors, sensor tubings, sensor cables, cord sensor or sensor fibres has a diameter of 1 mm or more than 0.5 mm, whereby the diameter of elongated sensors, sensor tubings, sensor cables, cord sensor or sensor fibres has a diameter of 1 between 0.7 and 1.2 mm, whereby the sensing material covered surface is about 0.30 $cm^2$, whereby volume to add when layers have approx. 100 micron is between 25-35 $cm^3$ and preferably 29-31 $cm^3$, whereby the matrix is a polymer with a density between 0.5 to 1.5 $g/cm^3$, preferably between 0.8 and 1.2 $g/cm^3$, more preferably 0.9 and 1.1 $g/cm^3$ and most preferably around 1 $g/cm^3$.

Other component choices are these whereby the monitor of present invention comprises a controller based on a software assisted measurement system and control algorithm. Hereby the controller can have a computer readable medium tangibly embodying computer code executable on a processor. Particular aspects hereby are a processor connected to provide a control signal to an actuator configured to signal or alarm the aqueous liquid spillage, or a processor is connected to provide a control signal to an actuator configured to alert pilot or third party, or the processor is connected to provide a control signal to an actuator configured to locate the aircraft aqueous liquid spillage defect.

In a preferred embodiment the controller of the monitor of present invention operates as a safety fuse for spilling aqueous liquids whereby the noise caused by small conductance variations that occur during operations (temperature variations, aging of adhesives etc) is disregarded by the processor but whereby an essentially loss of conductivity is regarded as an aircraft aqueous liquid spillage.

In another embodiment, the monitor according to the invention comprises further a memory for storing the information signals and at least one transmitter for transmitting information signals to a base station adapted to receive information signals. In a specific embodiment this base station is adapted to transmit interrogation signals. Furthermore additionally at least one transmitter can be formed by a transponder which is adapted to receive the interrogation signals and to transmit information signals stored in the memory in response to receiving an interrogation signal and furthermore the at least one transmitter or transponder can be adapted to receive and transmit signals in the ether or the at least the base station is adapted to receive and transmit signals via a telephone network or the transmitter or transponder is adapted for information communication via a mobile telephone network. This will enhance passenger's safety because the presence of spilled aqueous liquids is detectable at a very early stage.

A preferred embodiment of the invention concerns an aircraft comprising sensors which sensor comprises a composite comprise a conducting compound which is embedded in a hydrophilic matrix whereby the components are mixed in a ratio so that the composite is above the percolation threshold so that when the composite is exposed to a water humidity close to RH=100% or liquid water, the system takes up liquid until the conductivity is essentially lost. Hereby the increase of the resistance due to the ingress of water is monitored by a digital multi-channel multimeter that is equipped with appropriate data logging facilities.

Yet another preferred embodiment of the invention concerns a self monitoring floor comprising the monitor according to any one of the above described embodiments, further comprising 1) joining floor panels, 2) joints between the floor panels and eventually a sealing system between said floor panel joints, 3) a cover or protective coating and 4) a floor structure or a floor beam area.

The invention also concerns the use of the above described monitors of present invention. Particular uses of the monitor according to any one of the previous embodiments or of the self monitoring floor described here above, are 1) as a continuous or a intermediate but automated early warning system or sentinel for the prevention of corrosion by corrosive liquids; or 2) as a continuous or a intermediate but automated early warning system or sentinel for the prevention of corrosion by corrosive liquids; or 3) for in-situ providing continuous information and/or monitoring the presence of corrosive liquids so that corrosion treatment or corrosion prevention can start at a very early stage, or 4) to monitor the floor beam for hidden aqueous liquids in an aircraft for instance under a carpet or a protective coating of the floor beam, or 5) to protect underlying floor structure.

The monitor of present invention is particular suitable for a floor structure which comprises or is essentially composed of a corrosive material or for a floor structure which comprises or is essentially composed of aluminium alloys.

Particular and preferred aspects of the invention are set out in the accompanying independent and dependent claims. Features from the dependent claims may be combined with features of the independent claims and with features of other dependent claims as appropriate and not merely as explicitly set out in the claims.

Thus, the claims following the detailed description are hereby expressly incorporated into this detailed description, with each claim standing on its own as a separate embodiment of this invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

DETAILED DESCRIPTION

Detailed Description of Embodiments of the Invention

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

EXAMPLES

An organo-ceramic composite consisting of titaniumcarbonitride (TiCN) powder (70/30) and polyvinyl alcohol (PVA) was produced. The components were weighted in an appropriate ratio, i.e. the concentration was chosen that the system was above the percolation threshold. The weight percentage of TiCN was in the range of 80% which means that the volume fraction of TiCN was about 45% (density of TiCN about 6200 kg/m$^3$ and PVA about 1300 kg/m$^3$). Although, many different conducting compounds could be used for that sensor, a ceramic compound was selected because it is highly non-combustible in contrast to metal powders or graphite. This makes it a better material for aircraft applications. The matrix material (PVA), a polymer that is hygroscopic, i.e. it swells when it is exposed to a gaseous or liquid water phase. The components were mixed with an appropriate amount of water and sufficiently stirred until a homogenous substance was obtained.

Figure 2:
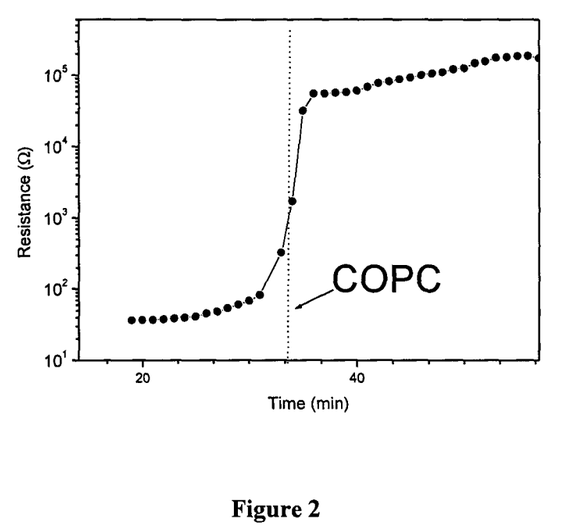
FIG. 2) is a graphic that displays the resistance of TiCN/PVA Composite (45 Vol %) after hydration according to the first set-up.
Figure 3:
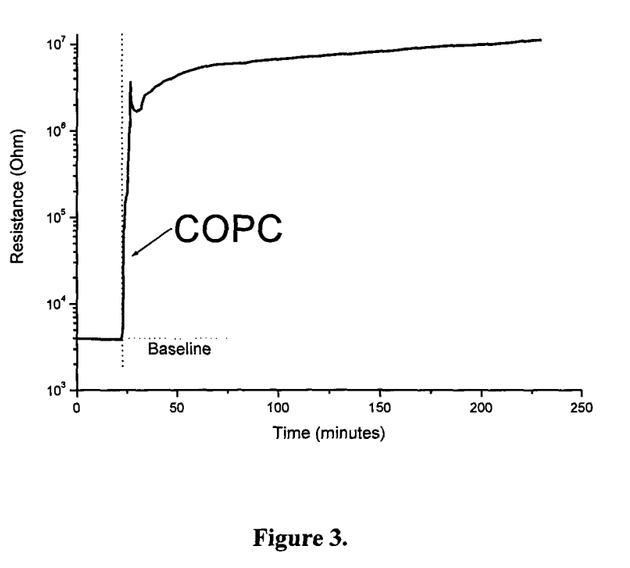
FIG. 3) is a graphic that displays the resistance of the TiCN/PVA sensor (45 Vol %) after exposing the complete sensor to a sample of cola.

First set-up: Using a syringe (where the components were mixed and homogenized before), a wire was drawn on an acrylic plate (width of about 2 mm and a length of 150 mm). The material at both ends was in direct contact with respective electrodes. The thickness was slightly varying and estimated to be in the range of 500 micrometer. After a drying time of 16 hours, the resistance was measured with a digital multimeter to be in the range of 25 Ohm. This means an estimated specific resistance of about 3000 S/m. After exposing a part of the wire to a water drop, the resistance grows gradually until the range of 100 Ohm. From this point on, a resistance jump occurred until the range of 100 kOhm and that jump could finally be identified as the percolation threshold. The final resistance was reached at about 600 kOhm. The corresponding specific resistance can be estimated to be in the range of 2 S/m. The curve shown in the diagram (FIG. 2) represents a kinetic process driven by the diffusion of water into the PVA matrix, i.e. when changing e.g. the mass of the sample, the initial water amount, exposed surface etc. the curve would change its kinetic parameters. Moreover, there are reasons to assume that the conductivity above the percolation threshold is not due to the percolated ceramic powder, but due to the ions dissolved in the aqueous phase that on its own has started to create a percolation network.

In a second set-up (figure 4), a new sample was prepared with the same specifications such as described above. The starting substance (PVA+TiCN+H$_2$O) was deposited on a cord of polyamides. That cord is sometimes implemented in aircraft floor beam sealings to enable a proper removal of the sealings between the floor beams during regular maintenance operations. Before deposition of the coating, an isolated electric wire was mounted into the core of the polyamide cord for the required electric connections. The composite was uniformly deposited on the polyamide cord using a specific vessel, i.e. deposition occurred when the cord was pulled through this vessel. At the edges, the composite was in contact with the flex wires of the electrical cable to establish a continuous circuit if resistance measurements are performed. We used about 4 g of raw material for the coating of 1 m of the polyamide cord. This gives an estimated thickness of the coating of about 400 micrometer. After 16 hours of drying, the resistance of 1 m sensor was in the range of 30 kOhm. After exposing the sensor to a coca-cola sample being a typical corrosive agent when spilled in aircraft areas, the resistance increases characteristically from about 30 kOhm to approximately 80 MOhm. Also here, the remaining resistance is most probably due to the ions dissolved in the aqueous phase that on its own has started to create a percolation network.

Figure 4:
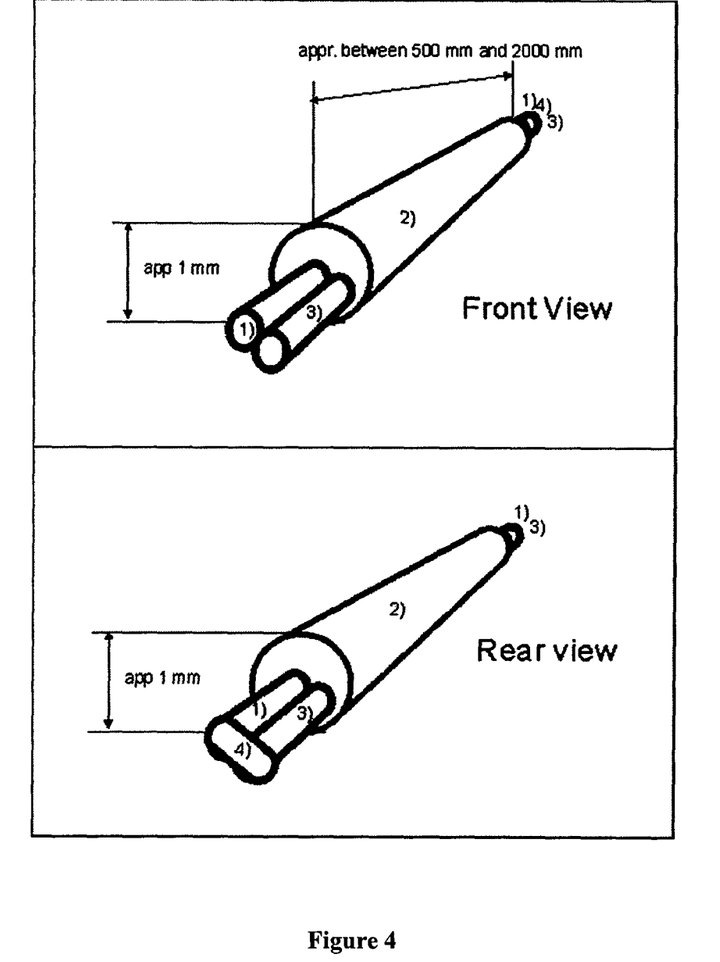
Figure 5:
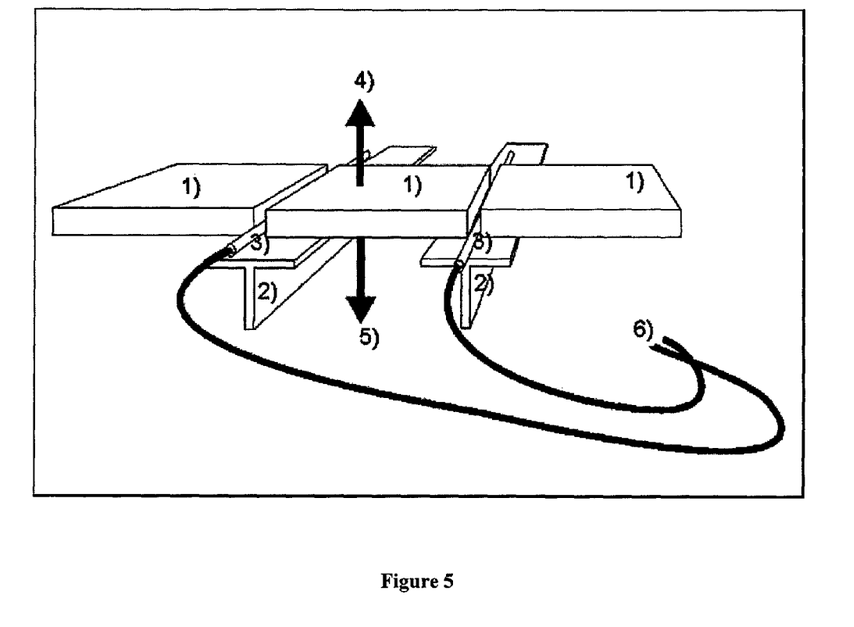

An important feature of this invention is the stability of the non-conducting state. Once, a relevant amount of liquid has entered the floor beam area, the sensor will absorb this liquid because ingressing liquid has to pass the positions of the sensor (FIGS. 4 and 5, drawings 1 and 2). The absorbed liquid interrupts the electrical contact at a certain position. Due to the relatively high sample amount, the thickness of the coating and the length of the sensor, the drying time of the sensor is extremely long, especially in the confined space of floor plate joints in aircraft. It could be shown that in a lab experiment, the extraordinary high resistance will be maintained for many days. This means that the read-out of the sensor must not necessary be done during flight operations, but it can be done by electronic devices that are not part of the operational electronics. This essentially reduces the certification efforts when implementing the sensors reducing the costs of the overall system.

DRAWING DESCRIPTION

Brief Description of the Drawings

The present invention will become more fully understood from the detailed description given herein below and the accompanying drawings which are given by way of illustration only, and thus are not limitative of the present invention, and wherein:

FIG. 4 is a drawing (Drawing 1) that displays an embodiment of a set-up of the floorbeam sensor, the length depend on requirements.
1) Electrical core consisting of isolated electric wire (if possible already certified, e.g. ASNE 0261-CF24U)
2) Coat consisting of a nylon cord (already available as certified for floorbeams) impregnated with COPC-based sensing composite (approx. 100 micron thickness)
3) Electrode to be connected with the COPC-based sensing composite (flex wires at the edges that are embedded in composite)
4) Shortcut between COPC-based sensing composite and electrical core FIG. 5 is a drawing (Drawing 2) that displays and embodiment of deposition of the sensor in the floorbeam area (carpet, sealing systems and possible seat tracks are not shown).
1) Floor plates
2) Floor beams
3) COPC-based sensor according to Drawing 1
4) Cabin area
5) Access to cargo area
6) Electrodes for resistance measurements during maintenance In interpreting these claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or function;
g) any of the disclosed devices or portions thereof may be combined together or separated into further portions unless specifically stated otherwise;
h) no specific sequence of acts is intended to be required unless specifically indicated; and
i) the term "plurality of" an element includes two or more of the claimed element, and does not imply any particular range of number of elements; that is, a plurality of elements can be as few as two elements.

What is claimed is:

1. A sensor to detect liquid spilling in a covered structure in a confined environment, comprising:
    a cord, an insulated electric wire mounted into a core of the cord, and a sensing composite coated onto an exterior surface of the cord;
    wherein the sensing composite comprises particles or powder of an electrically-conductive material dispersed in a matrix that is hydrophilic or that is highly solvable to aqueous fluids;
    the concentration, dispersion and/or orientation of the electrically conductive particles or powder are arranged to make the sensing composite electrically conductive in an ambient with relative humidity below about 70% and to increase an electrical resistance of the sensing composite above a threshold of percolation conductivity collapse after ingress of an aqueous liquid into the sensing composite; and
    wherein the electric wire and the sensing composite form a continuous electric circuit on which resistance measurements are performed, to indicate the presence of the spilled liquid.

2. The sensor of claim 1, wherein the matrix is arranged to swell after exposure to the aqueous liquid.

3. The sensor of claim 1, wherein the matrix comprises polyvinyl alcohol.

4. The sensor of claim 1, wherein the matrix is formed of a polymer having a density between 0.5 g/cm$^3$ and 1.5 g/cm$^3$.

5. The sensor of claim 1, wherein the particles or the powder of the electrically conductive material are made of a ceramic material.

6. The sensor of claim 1, wherein the particles or the powder of the electrically conductive material comprise titanium carbonitride.

7. The sensor of claim 1, wherein the particles or the powder of the electrically conductive material comprise nickel, silver, copper, graphite, or mixtures thereof.

8. The sensor of claim 1, wherein the cord is made of polyamide.

9. A monitoring apparatus to detect liquid spilling, comprising a plurality of sensors of claim 1, wherein the sensors are arranged to form an array.

10. An aircraft comprising a plurality of sensors of claim 1.

11. The aircraft of claim 10, comprising floor beams between a cabin area and a cargo area of the aircraft, and floor panels provided on the floor beams, wherein the sensors are arranged on the floor beams and in between the floor panels.

12. The aircraft of claim 11, wherein the sensors are arranged underneath a floor covering.

13. The aircraft of claim 10, comprising a wall structure, wherein the sensors are arranged on or against the wall structure.

14. The aircraft of claim 10, wherein the sensors are coupled to form a monitor for detecting liquid spilling.

15. A method of monitoring a floor or wall structure within an aircraft to detect ingress of aqueous liquids into the structure, comprising:
   providing an aircraft comprising a floor structure or a wall structure;
   providing a sensor comprising terminal connections and a sensing composite coated on a fiber, wherein:
      the sensing composite comprises particles or powder of an electrically conductive material dispersed in a matrix that is hydrophilic or that is highly solvable to aqueous fluids;
      the concentration, dispersion and/or orientation of the electrically conductive particles or powder are arranged to make the sensing composite electrically conductive in an ambient with relative humidity below about 70% and to increase an electrical resistance of the sensing composite above a threshold of percolation conductivity collapse after ingress of an aqueous liquid into the sensing composite; and
      the terminal connections are electrically connected to the sensing composite;
   mounting the sensor on the floor structure or the wall structure; and
   monitoring the electrical resistance of the sensor to detect when the electrical resistance exceeds the threshold.

16. The method of claim 15, comprising arranging the sensor underneath a floor or wall covering.

17. The method of claim 15, comprising arranging the sensor on the floor structure of a cabin area of the aircraft.

* * * * *